US010792191B2

(12) United States Patent
Robinson et al.

(10) Patent No.: US 10,792,191 B2
(45) Date of Patent: Oct. 6, 2020

(54) FOAM WOUND INSERTS WITH REGIONS OF HIGHER AND LOWER DENSITIES, WOUND DRESSINGS, AND METHODS

(71) Applicant: KCI Licensing, Inc., San Antonio, TX (US)

(72) Inventors: Timothy Mark Robinson, Shillingstone (GB); Paul Slack, Plantation, FL (US); Christopher Brian Locke, Bournemouth (GB); Ben Stokes, Ringwood (GB)

(73) Assignee: KCI Licensing, Inc., San Antonio, TX (US)

( * ) Notice: Subject to any disclaimer, the term of this patent is extended or adjusted under 35 U.S.C. 154(b) by 338 days.

(21) Appl. No.: 15/683,385

(22) Filed: Aug. 22, 2017

(65) Prior Publication Data

US 2017/0348153 A1    Dec. 7, 2017

Related U.S. Application Data

(63) Continuation of application No. 13/009,238, filed on Jan. 19, 2011, now Pat. No. 9,770,368.

(60) Provisional application No. 61/296,817, filed on Jan. 20, 2010.

(51) Int. Cl.
| | | |
|---|---|---|
| *A61F 13/00* | (2006.01) | |
| *B29C 44/56* | (2006.01) | |
| *A61M 1/00* | (2006.01) | |
| *B29L 31/00* | (2006.01) | |

(52) U.S. Cl.
CPC .. *A61F 13/00034* (2013.01); *A61F 13/00068* (2013.01); *A61F 13/00991* (2013.01); *B29C 44/5636* (2013.01); *A61F 2013/0017* (2013.01); *A61F 2013/0054* (2013.01); *A61F 2013/0074* (2013.01); *A61F 2013/00174* (2013.01); *A61F 2013/00327* (2013.01); *A61F 2013/00536* (2013.01); *A61F 2013/00544* (2013.01); *A61F 2013/00557* (2013.01); *A61M 1/0088* (2013.01); *B29L 2031/753* (2013.01)

(58) Field of Classification Search
CPC ................................................. A61F 13/00034
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

European Preliminary Examination Report for Corresponding Application No. 117350769, dated Mar. 13, 2018.

(Continued)

*Primary Examiner* — Larry W Thrower

(57) ABSTRACT

Foam wound inserts with high-density and low-density regions, methods for making wound inserts, wound-treatment methods, and wound-treatment systems.

6 Claims, 7 Drawing Sheets

(56) References Cited

U.S. PATENT DOCUMENTS

| | | |
|---|---|---|
| 3,367,332 A | 2/1968 | Groves |
| 3,520,300 A | 7/1970 | Flower, Jr. |
| 3,566,871 A | 3/1971 | Richter et al. |
| 3,568,675 A | 3/1971 | Harvey |
| 3,648,692 A | 3/1972 | Wheeler |
| 3,665,918 A | 5/1972 | Lindquist et al. |
| 3,682,180 A | 8/1972 | McFarlane |
| 3,826,254 A | 7/1974 | Mellor |
| 3,941,633 A | 3/1976 | Wang et al. |
| 3,975,567 A | 8/1976 | Lock |
| 3,977,406 A | 8/1976 | Roth |
| 3,978,266 A | 8/1976 | Lock |
| 3,978,855 A | 9/1976 | McRae et al. |
| 4,040,884 A | 8/1977 | Roth |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,259,569 A | 3/1981 | Passer et al. |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,409,976 A | 10/1983 | Pence |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,569 A | 7/1985 | Palau |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,210 A | 4/1987 | Edenbaum et al. |
| 4,655,754 A | 4/1987 | Richmond et al. |
| 4,664,662 A | 5/1987 | Webster |
| 4,690,953 A | 9/1987 | Orr et al. |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,080,661 A | 1/1992 | Lavender et al. |
| 5,086,170 A | 2/1992 | Luheshi et al. |
| 5,092,858 A | 3/1992 | Benson et al. |
| 5,098,500 A | 3/1992 | Reed et al. |
| 5,100,396 A | 3/1992 | Zamierowski |
| 5,134,994 A | 8/1992 | Say |
| 5,149,331 A | 9/1992 | Ferdman et al. |
| 5,164,421 A | 11/1992 | Kiamil et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,571,078 A | 11/1996 | Malewicz |
| 5,607,388 A | 3/1997 | Ewall |
| 5,636,643 A | 6/1997 | Argenta et al. |
| 5,645,081 A | 7/1997 | Argenta et al. |
| 5,782,787 A | 7/1998 | Webster |
| 5,973,221 A | 10/1999 | Collyer et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,368,702 B1 | 4/2002 | Erickson |
| 6,488,643 B1 | 12/2002 | Tumey et al. |
| 6,493,568 B1 | 12/2002 | Bell et al. |
| 6,509,388 B1 | 1/2003 | Addison |
| 6,528,697 B1 | 3/2003 | Knutson et al. |
| 6,553,998 B2 | 4/2003 | Heaton et al. |
| 6,610,897 B2 | 8/2003 | Cavanagh et al. |
| 6,720,470 B2 | 4/2004 | Cavanagh et al. |
| 6,803,495 B2 | 10/2004 | Simpson |
| 6,814,079 B2 | 11/2004 | Heaton et al. |
| 6,974,428 B2 | 12/2005 | Knutson et al. |
| 7,074,982 B2 | 7/2006 | Knutson et al. |
| 7,540,681 B2 | 6/2009 | Cybulski et al. |
| 7,651,484 B2 | 1/2010 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0062097 A1 | 5/2002 | Simpson |
| 2002/0077661 A1 | 6/2002 | Saadat |
| 2002/0095105 A1 | 7/2002 | Jensen |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0212358 A1 | 11/2003 | Cavanagh et al. |
| 2003/0229317 A1 | 12/2003 | Ferguson et al. |
| 2005/0020955 A1 | 1/2005 | Sanders et al. |
| 2005/0230638 A1 | 10/2005 | Ancona et al. |
| 2006/0004313 A1 | 1/2006 | Heinz et al. |
| 2006/0008633 A1 | 1/2006 | Chan et al. |
| 2006/0069380 A1 | 3/2006 | Chen et al. |
| 2007/0014837 A1 | 1/2007 | Johnson et al. |
| 2007/0147946 A1 | 6/2007 | Cybulski et al. |

(56) References Cited

U.S. PATENT DOCUMENTS

| | | |
|---|---|---|
| 2007/0161936 A1 | 7/2007 | Svetlik |
| 2007/0185426 A1 | 8/2007 | Ambrosio et al. |
| 2007/0253914 A1 | 11/2007 | Ha et al. |
| 2008/0200891 A1 | 8/2008 | Kim et al. |
| 2008/0213566 A1 | 9/2008 | Chan et al. |
| 2008/0275151 A1 | 11/2008 | Strandburg et al. |
| 2009/0054856 A1 | 2/2009 | Mormino et al. |
| 2009/0205649 A1 | 8/2009 | Tanaka et al. |
| 2009/0212454 A1 | 8/2009 | Smith et al. |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| CN | 1756570 A | 4/2006 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 1991015177 A1 | 10/1991 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 9963920 A1 | 12/1999 |
| WO | 2000035503 A1 | 6/2000 |
| WO | 2007136176 A1 | 11/2007 |

OTHER PUBLICATIONS

International Search Report issued in International Application No. PCT/US2011/021658 dated Sep. 26, 2011.

McNulty et al., "Effects of negative pressure wound therapy on cellular energetic in fibroblasts gorwn in a provisional mound (fibrin) matrix," Wound Repai and Regeneration, 17:192-199, 2009.

Vikatmaa et al., "Negative pressure wound therapy: a systematic review on effectiveness and safety," European Journal of Vascular and Endovascular Surgery, 36:438-448, 2008.

FeltCrest® compressed reticulated polyurethane foam, Crest Foam Industries, available online at http://www/crestfoam.com/bull102new.html, accessed Sep. 28, 2009.

Lyofoam™ Extra and Lyofoam™ Extra Adhesive Data Sheet, Molnlycke Health Care AB, available online at http://www.molnlycke.com/Documents/Wound%20care/LYOFOAM_EXTRA_AND_EXTRA_ADHESIVE/Documents/Global/15_08_LyofoamExtra_psm_UK.pdf, Accessed Sep. 28, 2009.

SIF Felt®—Permanently compressed reticulated foam polyester of polyether urethan, Foamex Technical Product Data Sheet, available online at http://www.steplaw.com/datasheets/Foamex?SIF_Felt.pdf, accessed Sep. 28, 2009.

European Search Report for EP11735076.9 dated Mar. 3, 2014.

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp: 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., MD., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by

(56) References Cited

OTHER PUBLICATIONS

V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

FOAM WOUND INSERTS WITH REGIONS OF HIGHER AND LOWER DENSITIES, WOUND DRESSINGS, AND METHODS

CROSS-REFERENCE TO RELATED APPLICATIONS

The present application is a continuation of U.S. patent application Ser. No. 13/009,238, entitled "Foam Wound Inserts With Regions of Higher and Lower Densities, Wound Dressings, and Methods," filed Jan. 19, 2011, which claims the benefit, under 35 USC § 119(e), of the filing of U.S. Provisional Patent Application No. 61/296,817, filed Jan. 20, 2010, which is incorporated herein in its entirety.

BACKGROUND

1. Field of the Invention

The present disclosure relates generally to healing of wounds and wound-treatment therapies. More particularly, but not by way of limitation, the present disclosure relates to fluid-instillation and negative-pressure wound therapies.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape).

SUMMARY

The present disclosure includes embodiments of wound inserts with high-density regions and low-density regions (e.g., unitary high-density regions and low-density regions), wound dressings, methods of making wound inserts, and wound-treatment methods.

Some embodiments of the present methods of making a wound insert, comprise: compressing at least a portion of a foam having thick portions and thin portions such that the compressed foam has a substantially constant thickness, and such that the thick portions have a density greater than the density of the thin portions; and treating the compressed foam such that the foam remains substantially compressed in the absence of an external compressive force.

In some embodiments, treating comprises heating the compressed foam to reduce the resiliency of the foam. In some embodiments, prior to compressing the foam, the thick portions and thin portions have substantially the same densities.

In some embodiments, treating comprises activating a coating that is distributed through at least a portion of the foam. In some embodiments, the coating is activated by heating the foam and the coating. In some embodiments, the coating comprises an adhesive. In some embodiments, the coating comprises a cross-linkable polymer, and where activating comprises exposing the coating to at least one of light and elevated temperature to cause at least some portion of the cross-linkable polymer to become cross-linked.

Some embodiments further comprise: cooling the foam; where cooling is performed after treating the compressed foam.

In some embodiments, the compressed thickness of the thick portions is substantially equal to the uncompressed thickness of the thin portions. In some embodiments, after being compressed the foam exhibits anisotropic properties.

Some embodiments of the present methods of making a wound insert, comprise: providing a foam including thick regions and thin regions having substantially the same densities; compressing at least a portion of the foam such that the foam has a substantially constant thickness, and such that the thick regions have a density greater than the density of the thin regions; heating the foam to an elevated temperature sufficient to reduce resiliency of the foam; and cooling the foam such that the compressed portion remains substantially compressed.

Some embodiments of the present methods of making a wound insert, comprise: compressing at least a portion of a foam such that the foam has a substantially constant thickness; heating the foam to an elevated temperature sufficient to reduce resiliency of the foam; and cooling the foam such that the compressed portion remains substantially compressed; where prior to being compressed, the foam includes thick regions and thin regions (e.g., unitary thick regions and thin regions) having substantially the same densities, and after being compressed the thick regions have a density greater than the density of the thin regions.

In some embodiments, the foam comprises an open-celled foam. In some embodiments, the foam comprises a hydrophilic (or hydrophobic) foam. In some embodiments, prior to being compressed the thick regions of the foam have a uncompressed thickness greater than the uncompressed thickness of the thin regions, and where the compressed thickness of the thick portions is substantially equal to the uncompressed thickness of the thin portions. In some embodiments, after being compressed the foam exhibits anisotropic properties.

Some embodiments of the present methods of making a wound insert comprise: providing a foam including thick regions and thin regions having substantially the same densities; compressing at least a portion of a foam such that the foam has a substantially constant thickness, and such that the thick regions have a density greater than the density of the thin regions; and activating a coating that is distributed through at least a portion of the foam such that the compressed portion remains at least partially compressed in the absence of an external compressive force.

Some embodiments of the present methods of making a wound insert comprise: compressing at least a portion of a foam such that the foam has a substantially constant thickness; and activating a coating that is distributed through at least a portion of the foam such that the compressed portion remains at least partially compressed in the absence of an external compressive force; where prior to being compressed, the foam includes thick regions and thin regions (e.g., unitary thick regions and thin regions) having substantially the same densities, and after being compressed the thick regions have a density greater than the density of the thin regions.

In some embodiments, the coating comprises an adhesive. In some embodiments, the coating comprises a cross-linkable polymer, and activating comprises exposing the coating to at least one of light and elevated temperature to cause at least some portion of the cross-linkable polymer to become cross-linked.

Some embodiments of the present wound inserts are for use with a wound dressing, and comprise: a foam having high-density regions and low-density regions. In some embodiments, the foam comprises a hydrophilic foam. In some embodiments, the high-density regions and low-density regions are configured in alternating rows. In some embodiments, the high-density regions and low-density regions are configured in a grid pattern.

Some embodiments of the present wound dressings are for healing wounds using negative pressure wound therapy, and comprise: any of the present wound inserts; and a drape for coupling to skin of a patient adjacent the wound to which the dressing is applied such that the drape covers the wound insert and the wound, and forms a space between the drape and the wound.

Some embodiments of the present wound inserts (e.g., for use with a wound dressing) comprise: a foam (e.g., sterile foam) having high-density regions and low-density regions having a density that is less than the density of the high-density regions. In some embodiments, the foam is formed by any of the present methods. In some embodiments, the foam comprises a hydrophilic (or hydrophobic) foam. In some embodiments, the high-density regions and low-density regions are configured in alternating rows. In some embodiments, the high-density regions and low-density regions are configured in a grid pattern.

Some embodiments of the present wound dressings comprise: a wound insert configured to be positioned on a wound of a patient, the wound insert comprising a foam (e.g., sterile foam) having high-density regions and low-density regions having a density that is less than the density of the high-density regions; and a drape configured to be coupled to skin of the patient adjacent the wound such that the drape covers the wound insert and the wound, and forms a space between the drape and the wound.

Some embodiments of the present wound-treatment methods comprise: positioning a wound insert on a wound of a patient, the wound insert comprising a sterile (e.g., sterile) foam having high-density regions and low-density regions having a density that is less than the density of the high-density regions; and coupling a drape to skin adjacent the wound such that the drape covers the wound insert and the wound, and forms a space between the drape and the wound. Some embodiments further comprise: applying negative pressure to the wound through the wound dressing. In some embodiments, applying negative pressure comprises activating a vacuum source that is coupled to the wound dressing. Some embodiments further comprise: delivering a fluid to the wound through the wound dressing. In some embodiments, delivering a fluid comprises activating a fluid source that is coupled to the wound dressing.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises a wound insert and a drape, the wound dressing includes the specified elements but is not limited to having only those elements. For example, such a wound dressing could also include a connection pad configured to be coupled to a wound-treatment apparatus.

Further, a device or structure that is configured in a certain way is configured in at least that way, but it can also be configured in other ways than those specifically described.

Figure 1:
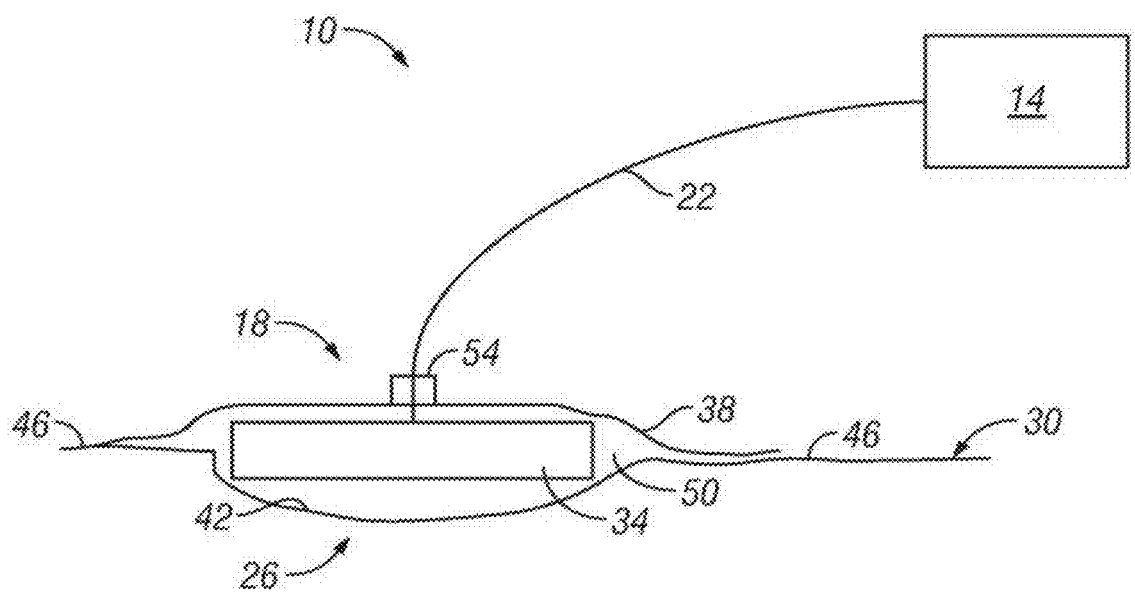
FIG. 1 depicts a side view of one embodiment of the present wound dressings having one of the present wound inserts and coupled to a wound site and to a wound treatment apparatus.

Referring now to the drawings, and more particularly to FIG. 1, shown therein is an embodiment of one of the present wound treatment system 10. In the embodiment shown, apparatus 10 comprises a wound-treatment apparatus 14, and a wound dressing 18 coupled to apparatus 14 by a conduit 22. As shown, dressing 18 is configured to be coupled to (and is shown coupled to) a wound 26 of a patient 30. More particularly, in the embodiment shown, dressing 18 comprises a wound insert 34 and a drape 38. As shown, wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers wound insert 34 and wound 26, and forms a space 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (e.g., an installation fluid such as a medicinal fluid, antibacterial fluid, irrigation fluid, and or the like) to wound dressing 18. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A., and/or its subsidiary and related companies (collectively, "KCI").

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, a first lumen for the application of negative pressure and/or fluid delivery, and at least one additional lumen for coupling to pressure sensor(s) to sense pressure or negative pressure between drape 38 and surface 42. In some embodiments, conduit 22 can comprise multiple lumens (e.g., as in a single conduit with a central lumen for application of negative pressure and/or fluid delivery, and one or more peripheral lumens disposed adjacent or around the central lumen such that the peripheral lumens can be coupled to a pressure sensor to sense a pressure or negative pressure between drape 38 and surface 42 (e.g. in space 50). The lumens may be arranged with a central lumen and other lumens disposed radially around the central lumen, or in other suitable arrangements. The lumens may also be provided in separate conduits. In the embodiment shown, system 10 further comprises a wound dressing connection pad 54 configured to be coupled to (and is shown coupled to) conduit 22. One example of a suitable connection pad 54 is the "V.A.C. T.R.A.C.® Pad," commercially available from KCI. One example of a suitable drape 38 includes the "V.A.C.® Drape" commercially available from KCI.

Figure 2:
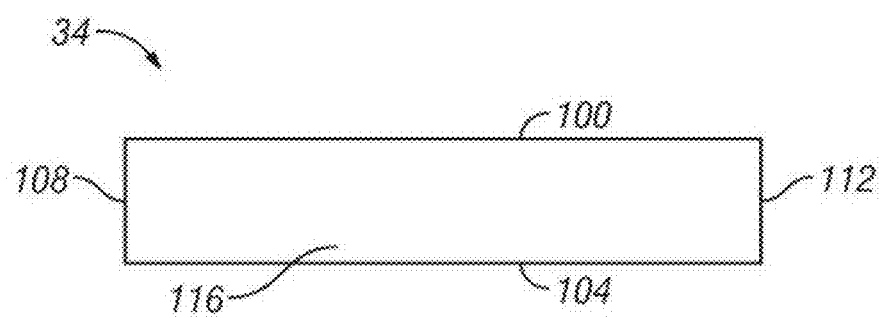
FIG. 2 depicts an enlarged side view of the wound insert of FIG. 1.

Referring now to FIG. 2, a side view of a wound insert 34 is shown. Wound insert 34 has an upper side 100, a lower side 104, lateral sides 108, 112 and interior volume 116. Although only one side is shown of wound insert 34, it will be understood by those of ordinary skill in the art that wound insert 34 includes a three-dimensional rectangular volume having a depth extending perpendicular to the side shown. In other embodiments, wound insert 34 can have any suitable shape, such as, for example, a round cylindrical shape, a fanciful shape, or may be trimmed to fit an irregular shape of a wound (e.g., 26 and/or wound surface 42). Wound insert 34 can comprise a foam, such as, for example, open-celled foam (which may also be reticulated).

Figure 3:
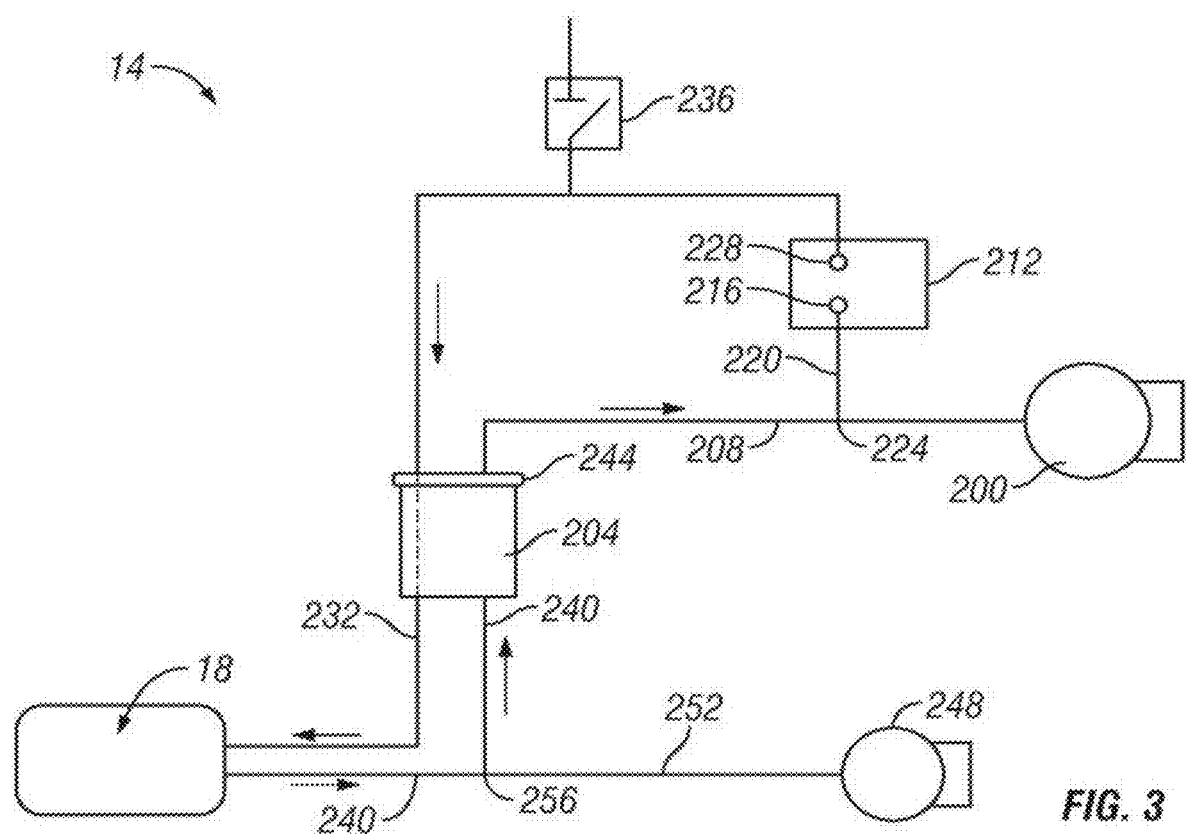
FIG. 3 depicts a schematic block diagram of one embodiment of a wound treatment apparatus that can comprise and/or be coupled to and/or be used with the present wound dressings and/or wound inserts.

Embodiments of the present wound treatment methods may be better understood with reference to FIG. 3, which depicts a schematic block diagram of one embodiment of system 10. In the embodiment shown, wound dressing 18 is coupled to apparatus 14, and apparatus 14 comprises a vacuum source 200 (e.g., a vacuum pump and/or the like) coupled to a canister 204 (e.g., configured to receive exudate and or the like from wound dressing 18) by way of a conduit 208. In the embodiment shown, apparatus 14 further comprises: a pressure sensor 212 having a first pressure transducer 216 coupled to conduit 208 by way of conduit 220 and/or tee-fitting 224, and a second pressure transducer 228 coupled to canister 204 and/or wound dressing 18 by way of conduit 232. Pressure sensor 212 is configured to sense the negative pressure in wound dressing 18, and/or any of the various lumens (e.g., within conduits) coupled to wound dressing 18, pressure sensor 212, and/or vacuum source 200.

In the embodiment shown, apparatus 14 further comprises a pressure release valve 236 coupled to conduit 232. Further, in the embodiment shown, canister 204 and vacuum source 200 are coupled to wound dressing 18 by way of conduit 240; and/or canister 204 can comprise a filter 244 at or near an outlet of canister 204 to prevent liquid or solid particles from entering conduit 208. Filter 244 can comprise, for example, a bacterial filter that is hydrophobic and/or lipophilic such that aqueous and/or oily liquids will bead on the surface of the filter. Apparatus 14 is typically configured such that, during operation, vacuum source 200 will provide sufficient airflow through a filter 244 that the pressure drop across filter 244 is not substantial (e.g., such that the pressure drop will not substantially interfere with the application of negative pressure from wound dressing 18 from vacuum source 200).

In the embodiment shown, apparatus 14 further comprises a fluid source 248 coupled to wound dressing 18 by way of a conduit 252 that is coupled to conduit 240 such as, for example, by way of a tee- or other suitable fitting 256. In some embodiments, tee fitting 256 can comprise a switch valve and/or the like such that communication can be selectively permitted between wound dressing 18 and vacuum source 200, or between wound dressing 18 and fluid source 248. In some embodiments apparatus 14 comprises only one of vacuum source 200 and fluid source 248. In embodiments of apparatus 14 that comprise only fluid source 248, canister 204 and/or pressure sensor 212 can also be omitted. In various embodiments, such as the one shown, conduit 232 and/or conduit 240 and/or conduit 252 can be combined and/or comprised in a single multi-lumen conduit, such as is described above with reference to FIG. 1. In some embodiments, fluid source 248 is coupled directly to wound dressing 18 (e.g., conduit 252 is coupled one end to wound dressing 18, such as via connection pad 54, and conduit 252 is coupled on the other end to fluid source 248; and conduit 252 is not coupled to tee fitting 256).

In various embodiments, such as the one shown in FIG. 3, apparatus 14 can be configured such that as soon as liquid in the canister reaches a level where filter 244 is occluded, a much-increased negative (or subatmospheric) pressure occurs in conduit 208 and is sensed by transducer 216. Transducer 216 can be connected to circuitry that interprets such a pressure change as a filled canister and signals this by means of a message on an LCD and/or buzzer that canister 204 requires emptying and/or replacement, and/or that automatically shuts off or disables vacuum source 200.

Apparatus 14 can also be configured to apply negative (or subatmospheric) pressure (e.g., continuously, intermittently, and/or periodically) to the wound site, and/or such that pressure relief valve 236 enables pressure at the wound site to be brought to atmospheric pressure rapidly. Thus, if apparatus 14 is programmed, for example, to relieve pressure at ten-minute intervals, at these intervals pressure relief valve 236 can open for a specified period, allow the pressure to equalize at the wound site, and then close to restore the negative pressure. It will be appreciated that when constant negative pressure is being applied to the wound site, valve 236 remains closed to prevent leakage to or from the atmosphere. In this state, it is possible to maintain negative pressure at the wound site without running and/or operating pump 200 continuously, but only from time to time or periodically, to maintain a desired level of negative pressure (i.e. a desired pressure below atmospheric pressure), which is sensed by transducer 216. This saves power and enables the appliance to operate for long periods on its battery power supply.

Figure 4:
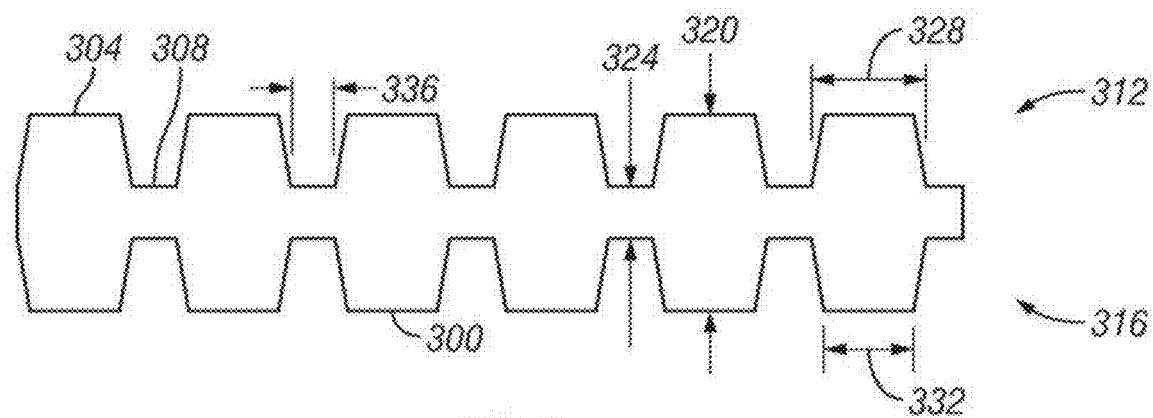
FIG. 4 depicts an end view of an embodiment of the present wound inserts.

Referring now to FIGS. 4-7, various views are shown of several embodiments of the present wound inserts. FIG. 4 depicts an end view of a foam 300 that includes thick regions 304 and thin regions 308. In the embodiment shown, thick regions 304 and thin regions 308 are unitary (i.e., are included and defined in a single piece of foam). As shown, the foam is substantially uncompressed such that thick regions 304 and thin regions 308 have substantially the same density. Foam 300 can comprise an open-celled foam (which may also be reticulated), and/or may be hydrophilic and/or hydrophobic. Foam 300 has a trapezoidal configuration in which each thick portion 304 has a trapezoidal shape on each side of thin portions 308. More particularly, each thick portion 304 has an upper side 312 and a lower side 316, and each has a trapezoidal shape extending from thin portions 308. In other embodiments, thick portions 304 may extend from only a single side of thin portions 308 (e.g., only have upper side 312 or lower side 316). In other embodiments, upper and/or lower sides 312, 316 of each thick portion 304 can have any shape that permits foam 300 to be compressed, treated, or used as described in this disclosure, such as, for example, square, rectangular, triangular, arcuate, hemispherical, or the like.

Thick regions 304 have a thickness 320 that is larger or thicker than a thickness 324 of thin regions 308. For example, thickness 320 of thick regions 304 can be equal to, greater than, less than, or between any of: 120, 140, 160, 180, 200, 220, 240, 260, 280, 300, 320, 340, 360, 380, and/or 400 percent of thickness 324 of thin regions 308. For example, in some embodiments, thickness 320 is between 200 and 300 percent of thickness 324, such that, if compressed, to thickness 320, thick region 304 will have a density of between 2 and 3 times the density of thin region 308. Thick regions 304 also have a base width 328 (measured at the base of thick region 304 and top of thin regions 308), and a top width 332. In the embodiment shown, top width 332 is less than base width 328, and more particularly, top width 332 is between 70 and 80 percent of base width 328. In other embodiments, top width 332 can be equal to, less than, greater than, or between any of: 0, 10, 20, 30, 40, 50, 60, 70, 80, 90, and/or 100 percent of base width 328. Further, thin regions 308 have a width 336 that, in the embodiment shown, is between 30 to 40 percent of base width 328 of thick portions 304. In other embodiments, width 336 can be equal to, greater than, less than, or between any of: 10, 20, 30, 40, 50, 60, 70, 80, 90, 100, 120, 140, 160, 180, and/or 200 percent of base width 328. For example, in some embodiments, width 336 is between 20 and 50 percent of width 328 such that if compressed, foam 300 will have less low-density regions than high-density regions, and such that the high-density regions wick or draw fluids away from a large wound area, and the low-density regions permit communication of negative pressure to the wound surface.

Figure 5:
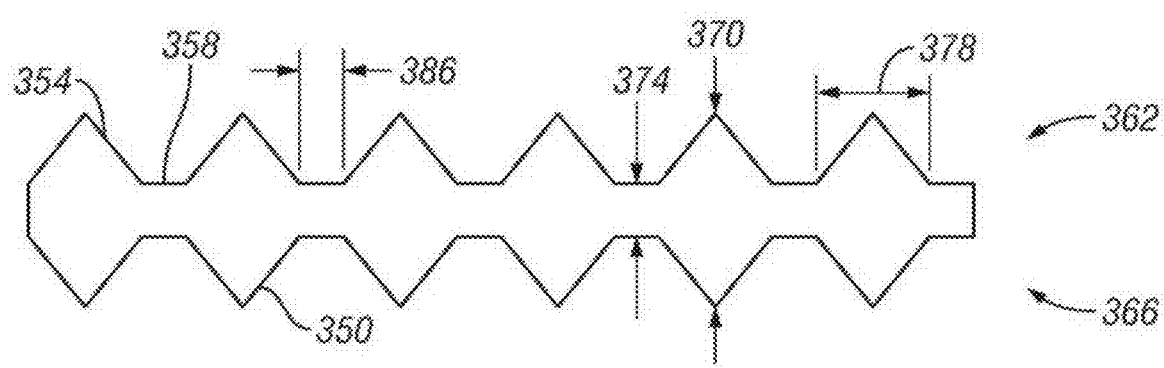
FIG. 5 depicts an end view of another embodiment of the present wound inserts.

FIG. 5 depicts an end view of another foam 350 including thick regions 354 and thin regions 358 (in the embodiment shown, thick and thin regions 354, 358 are included and defined in a single piece of foam). As shown, foam 350 is substantially uncompressed such that thick regions 354 and thin regions 358 have substantially the same density. Foam 350 comprises an open-celled foam (which may also be reticulated), such as, for example, a hydrophilic (or hydrophobic) foam. Foam 350 has a sawtooth configuration in which each thick portion 354 has a triangular shape on each side of thin portions 358. More particularly, each thick portion 354 has an upper side 362 and a lower side 366, and each has a triangular shape extending from thin portions 358. In other embodiments, thick portions 354 may extend from only a single side of thin portions 358 (e.g., only have upper side 362 or lower side 366). In other embodiments, upper and/or lower sides 362, 366 of each thick portion 354 can have any shape that permits foam 300 to be compressed, treated, or used as described in this disclosure, such as, for example, square, rectangular, arcuate, hemispherical, or the like.

Thick regions 354 have a thickness 370 that is larger or thicker than a thickness 374 of thin regions 358. For example, thickness 370 of thick regions 354 can be equal to, greater than, less than, or between any of: 120, 140, 160, 180, 200, 220, 240, 260, 280, 300, 320, 340, 360, 380, and/or 400 percent of thickness 374 of thin regions 358. Thick regions 354 also have a base width 378 (measured at the base of thick region 354 and top of thin regions 358). In the embodiment shown, thick portions 354 have a substantially triangular shape such that the width (top width) of each thick portion at the point furthest from thin portions 358 is substantially zero. Thin regions 358 have a width 386 that, in the embodiment shown, is between 30 to 40 percent of base width 378 of thick portions 354. In other embodiments, width 386 can be equal to, greater than, less than, or between any of: 10, 20, 30, 40, 50, 60, 70, 80, 90, 100, 120, 140, 160, 180, and/or 200 percent of base width 378.

Figure 6:
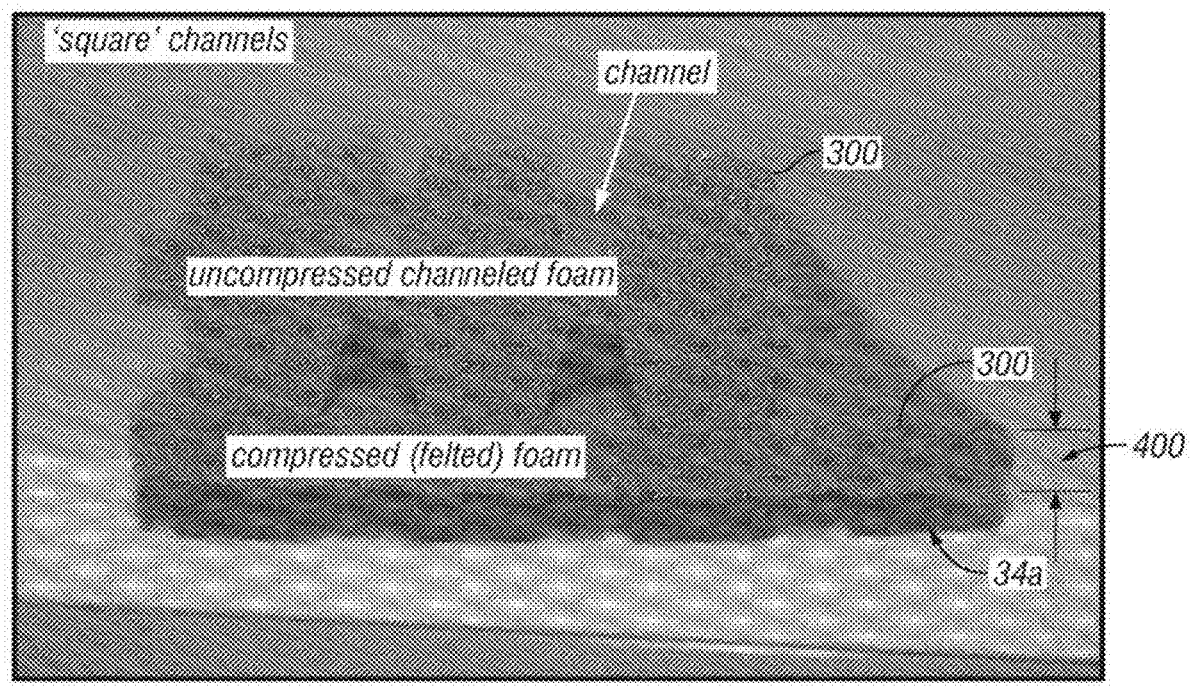
FIG. 6 depicts an end view photograph of an embodiment of the present wound inserts in uncompressed and compressed configurations.

FIG. 6 depicts an end perspective photograph of foam 300 in an uncompressed configuration such as that of FIG. 4, and in a compressed configuration in which foam 300 is configured as a wound insert 34a. As understood with reference to FIG. 6, some embodiments of the present methods of making wound inserts comprise: compressing (and/or felting) at least a portion of a foam (e.g., foam 300) such that the foam has a substantially constant thickness (e.g., thickness 400). Some embodiments comprise: treating (e.g., by applying heat, or activating a coating that has been applied to) the compressed foam such that the foam remains substantially compressed in the absence of an external compressive force. For example, in some embodiments, treating comprises heating the foam (e.g., foam) to an elevated temperature sufficient to reduce resiliency of the foam. For example, the foam can be heated to a temperature at which resiliency of the foam is reduced and/or relaxed, but that is below the melting temperature of the foam (e.g., such that the foam is not degraded by the elevated temperature). In this way, the foam can be compression set using heat and pressure (compressive force) to relax compressive strains developed in the foam. Generally, high temperatures are used to achieve the compression set. Examples of foam materials can include polyurethane (e.g., polyethers and/or polyesters), which may be hydrophobic or hydrophilic. To achieve the desired "set" such that resiliency of the foam is reduced and/or the foam remains substantially compressed in the absence of a compressive force, temperatures can range from 158 degrees Fahrenheit to 482 degrees Fahrenheit (e.g., equal to, less than, greater than, or between any of: 140, 160, 180, 200, 220, 240, 260, 280, 300, 320, 340, 360, 380, 400, 420, 440, 460, 480, 500 degrees Fahrenheit, depending upon the particular foam used). The foam may also be put through a cooling cycle to help retain the set introduced. For example, the foam may be cooled to a temperature below room or ambient temperature (e.g., to or in a temperature equal to, less than, greater than, or between any of: 0, 5, 10, 15, 20, 25, 30, 35, 40, 45, 50, 55, 60, 65, or 70 degrees Fahrenheit). In some embodiments of the present methods of forming a wound insert, the foam (e.g., foam 300) is disposed between two heated plates or platens (e.g., in a plate or platen press and/or where the plates are heated to a temperature sufficient to reduce the resiliency of the foam); and the press is actuated to move the plates toward one another (e.g., perpendicular to thickness 320 of thick portions 304) such that the foam is compressed to the desired overall thickness or degree of compression). Such a press can be electrically, mechanically, and/or hydraulically operated. Other foams that may be suitable include cross-linked and/or uncrosslinked polyolefin's, ethylene vinyl acetate (EVA), and elastomers such as acrylonitrile butadiene (NBR), polychloroprene (PCP or CR), ethylene propylene rubber (EPR & EPDM), silicones, and fluoro carbon polymers.

Some embodiments of the present methods of making wound inserts also comprise: cooling the foam (e.g., after heating the foam) such that the compressed portion of the foam remains substantially compressed at room temperature (e.g., at a temperature of 72 degrees Fahrenheit) in the absence of a compressive force. In other embodiments, cooling the foam includes cooling a coating that has been applied to the foam such that the compressed portion remains substantially compressed in the absence of a compressive force at a temperature or temperature range equal to, less than, greater than, or between any of: 10, 20, 30, 40, 50, 60, 70, 80, 90, 100, 110, 120, 130, 140, and/or 150 degrees Fahrenheit. In some embodiments, prior to being compressed, the foam (e.g., 300) includes thick regions (e.g., 304) and thin regions (e.g., 308) having substantially the same densities, and/or any other characteristics described above for foams 300 or 350 with reference to FIGS. 4 and 6; and after being compressed, the thick regions (e.g., 304) have a density greater than the density of the thin regions (e.g., 304).

Figure 9:
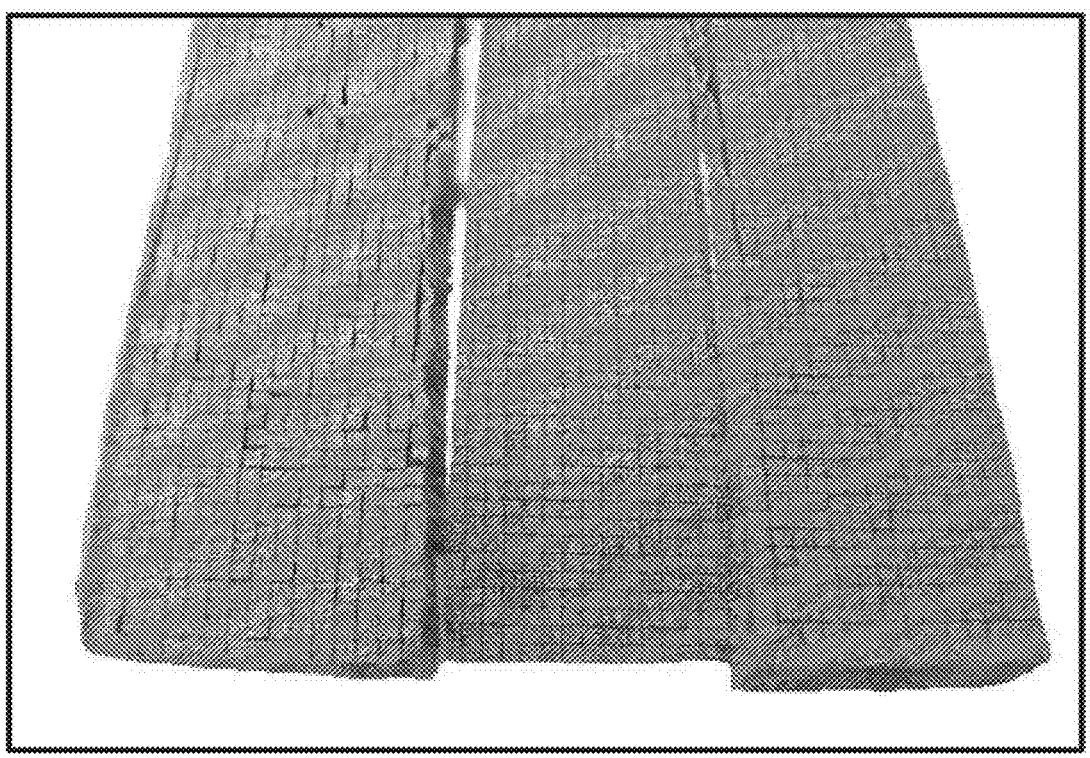
FIG. 9 depicts foam suitable for embodiments of the present wound inserts that has been cut by laser methods.

Thick and thin regions (e.g., 304, 308 and 354, 358) in the foam can be formed by any suitable methods, such as, for example, laser cutting or the like. For example, FIG. 9 shows a photograph of sheets of foam that have been cut in grid patterns by laser cutting, in a configuration that may be a precursor to certain of the present embodiments. For example, in the embodiment shown, portions of the sheets of foam may be removed along the grid pattern to define the thick portions and thin portions described above.

In some embodiments, the foam is compressed such that thickness 400 of the compressed foam 300 is substantially equal to the pre-compressed thickness 324 of thin portions 308. In other embodiments, the foam is compressed such that thickness 400 of the compressed foam 300 (wound insert 34a) is equal to, less than, greater than, or between any of: 50, 55, 60, 65, 70, 75, 80, 85, 90, 95, and 100 percent of thickness 324 of pre-compressed thin portions 308. In other embodiments, foam 300 is compressed such that only thick portions 304 are compressed and thickness 400 of the compressed foam 300 (wound insert 34a) is greater than thickness 324 of pre-compressed thin portions 308.

Other embodiments of the present embodiments of making wound inserts comprise: compressing at least a portion of a foam (e.g., 300) such that the foam (e.g., 300) has a substantially constant thickness (e.g., 400). In some embodiments, treating the foam comprises: activating a coating (e.g., a liquid coating such as adhesive or the like) that is applied to or distributed through at least a portion of the foam (e.g., 300) such that the compressed portion remains at least partially compressed (e.g., remains substantially compressed) in the absence of an external compressive force, such as at room temperature (e.g., at a temperature of 72 degrees Fahrenheit). For example, in some embodiments, a coating (e.g., an adhesive or cross-linkable polymer fluid) can be applied to the foam before or after compressing the foam, such that the coating can be activated (e.g., dried or activated with UV light) to substantially maintain the compression of the foam. In other embodiments, activating a coating includes activating the coating such that the compressed portion remains substantially compressed in the absence of a compressive force at a temperature or temperature range equal to, less than, greater than, or between any of: 10, 20, 30, 40, 50, 60, 70, 80, 90, 100, 110, 120, 130, 140, and/or 150 degrees Fahrenheit. In some embodiments, prior to being compressed, the foam (e.g., 300) includes thick regions (e.g., 304) and thin regions (e.g., 308) having substantially the same densities, and/or any other characteristics described above for foams 300 or 350 with reference to FIGS. 4 and 6; and after being compressed, the thick regions (e.g., 304) have a density greater than the density of the thin regions (e.g., 304).

In some embodiments, the foam is compressed such that thickness 400 of the compressed foam 300 is substantially equal to the pre-compressed thickness 324 of thin portions 308. In such embodiments, the coating can be dispersed through the foam, such as, for example, by spraying the foam with the coating, dipping the foam in the coating, and/or any other suitable way of dispersing the coating in the foam. In some embodiments, for example, the foam can be coated with a material that has a transition temperature (e.g., melting point, glass transition, etc.) that occurs at a relatively low temperature (e.g., lower than the foam alone), or that develops stiffness as it dries. In some embodiments, the coating can be configured to enable the foam to be compressed (and/or compression set) at lower temperatures (e.g., without heating), such that the coating becomes stiff or otherwise resistant to expansion as it cools or dries to hold the foam in its compressed configuration. For example, a fluid adhesive may be applied to thick portions before compressing the foam and permitted to dry before removing the compressive force, such that the dried adhesive will resist expansion from the compressed thickness. In other embodiments, the coating can be configured to compression set the foam such that the compression is reversible (e.g., at least partially and/or completely reversible) such that the foam can expand (e.g., after placing in or on a wound) as it warms or absorbs water. In some embodiments, the coating comprises a cross-linkable polymer and/or activating comprises exposing the coating to light and/or elevated temperature (e.g., above ambient temperature, such as, for example, a temperature sufficient to cause at least part of the cross-linkable polymer to cross-link) to cause at least some portion of the cross-linkable polymer to become cross-linked.

Examples of suitable coatings include cross-linkable polymers that contain n-methylol acrylamide (NMA). NMA is a monomer that may be co-polymerized with many other monomers (such as acrylics & vinyls). On heating, (e.g., to about 140° C.), NMA reacts with itself and other hydroxyl-containing groups (e.g., carboxyl). Similarly, urea formaldehyde, melamine formaldehyde, and/or phenol formaldehyde can be caused to react with themselves and other hydroxyl-containing polymers to form crosslinks. Other crosslinking agents may include, for example, modified ethylene ureas, which react with hydroxyl-containing polymers at elevated temperatures to crosslink them. Other crosslinking agents can include peroxides which will cross-link most polymers at elevated temperatures. Polymers containing hydroxyl and carboxyl groups may also be combined, and, when heated, may form polyester crosslinks. Additionally, epoxy prepolymers can be used that have low reactivity at room temperatures, and when heated, react quickly to form an epoxy polymer with crosslinks. Similarly, polymeric isocyanates may be used that will only react significantly fast at elevated temperatures and in presence of hydroxyl groups, amines, or moisture to form polyurethanes or polyureas.

Figure 7:
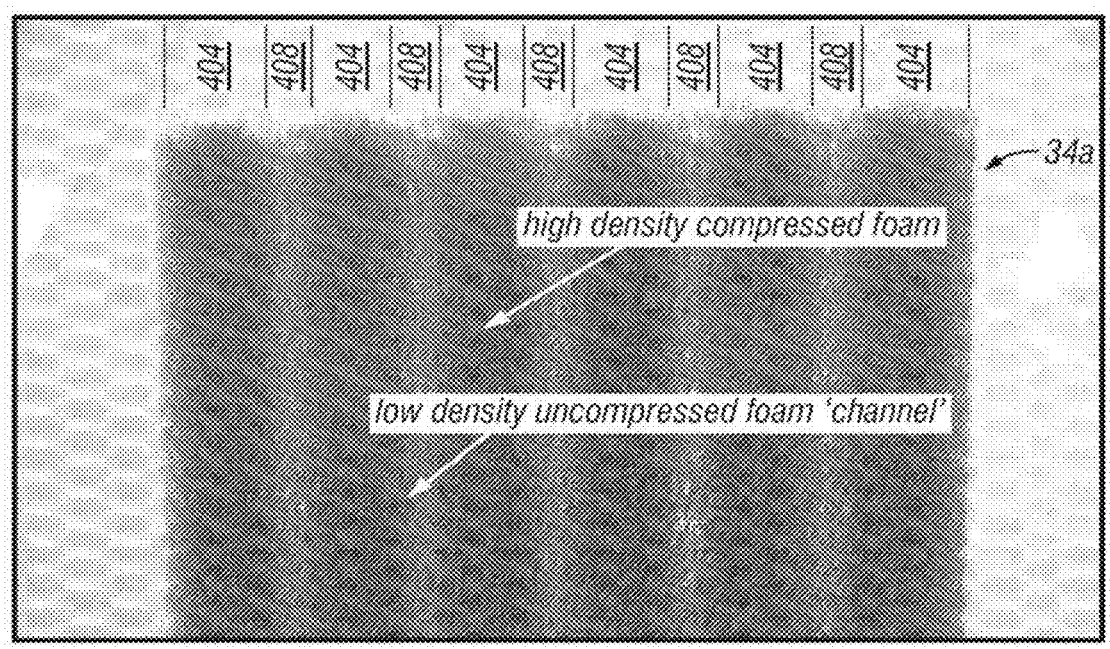
FIG. 7 depicts a top view photograph of the wound insert of FIG. 6 in a compressed configuration.

FIG. 7 illustrates a side view of wound insert 34a (compressed foam 300). As shown, after being compressed, the density of thick regions 304 increases because the foam material of thick regions 304 is compressed into a smaller space. As a result, wound insert 304 comprises compressed foam 300 (at least partially compressed—thin portions 308 may not be compressed at all) having high-density regions 404 and low-density regions 408 having a density that is less than the density of the high-density regions. More particularly, in the embodiment shown, high-density regions 404 and low-density regions are configured in alternating rows. In other embodiments, high-density regions 404 and low-density regions can be configured in any suitable pattern, such as, for example, a grid pattern or the like. The present wound inserts can be formed by any of the present methods described above.

The combination of high-density regions (e.g., 404) and low-density regions (e.g., 408) cooperate to provide various characteristics for the present wound inserts. For example, the high-density regions have a smaller aggregate cell size and increased cell density, such that the high-density regions have improved wicking function and more-effectively transmit fluid (e.g., draw fluids away from the wound surface and/or communicate fluid from a fluid source to the wound surface more effectively than the low-density regions. The high-density regions are generally also mechanically stronger than the low-density regions, such that the high-density regions can provide structural support for the low-density regions and/or the wound insert as a whole (e.g., such that the wound insert is resistant to tearing in directions that are not parallel to the low-density regions). Additionally, the low-density regions have a larger effective cell or pore size such that the low-density regions are less-susceptible to clogging. Especially when a negative pressure is applied to draw fluid and/or exudate away from the wound and through the wound insert, the larger pore size of the low-density regions may permit fluids to be drawn through the low-density regions at a higher velocity than the fluid is drawn through the high-density regions, such that particulate and granular matter are drawn to and/or through the low-density to discourage and/or decrease the likelihood of clogging in the high-density regions. In some embodiments, the foam can also be coated with a hydrophilic material to improve wicking properties of the wound insert.

The low-density regions may also be configured to permit the wound dressing to bend and/or otherwise conform to a wound. For example, the low-density regions can be relatively easier to bend (and/or less resilient when the wound insert is bent or folded along a low-density region) such as to double over a wound insert, and/or to conform a wound insert to additional hardware such as plates, pins, or the like. Typical single-density foam wound inserts are isotropic such that under negative pressure, a typical single-density foam wound insert will contract proportionally in all directions. In contract, the present wound inserts are configured to be anisotropic, such that the present wound inserts can be configured to mechanically assist with wound closure. For example, low-density regions 408 are less-dense (and will compress more under negative pressure) than high-density regions. As such, in the embodiment of FIG. 7, if negative pressure is applied to wound insert 34a, low density regions 408 will contract more than high-density regions 404, such that high-density regions 404 will be drawn together and wound insert 34a will contract laterally (perpendicular to the rows of regions 404, 408) more than longitudinally. As noted, the present wound inserts can be configured to have such anisotropic properties, and the present methods can employ such anisotropic properties, to mechanically assist closure of a wound, and/or apply other therapeutic strains to the wound (e.g., wound surface), while simultaneously applying a negative pressure to the wound and/or delivering fluids to the wound. For example, in other embodiments, the present wound inserts can be configured to have alternating and sequentially larger closed ring-shaped high-density regions 404 and low-density regions 408, such that under negative pressure, the wound insert will contract laterally inward to its own center.

Figure 8A:
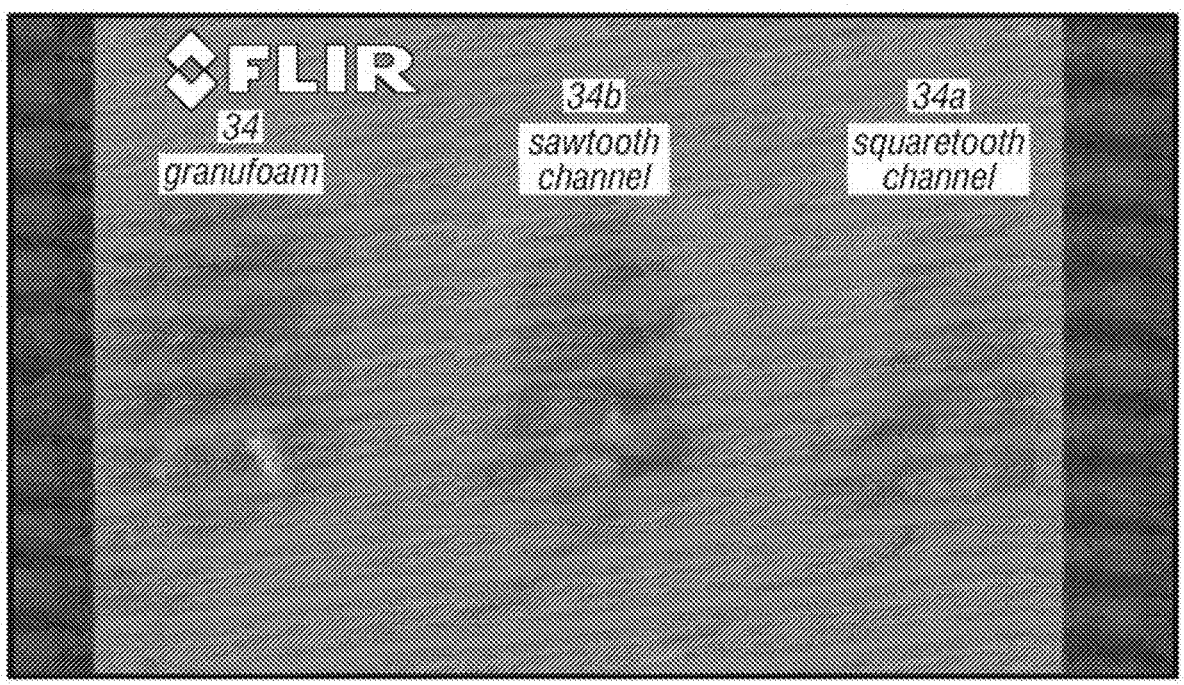
FIGS. 8A and 8B depict forward looking infrared FLIR images of fluid migration through embodiments of the present wound inserts and through a prior art wound insert.
Figure 8B:
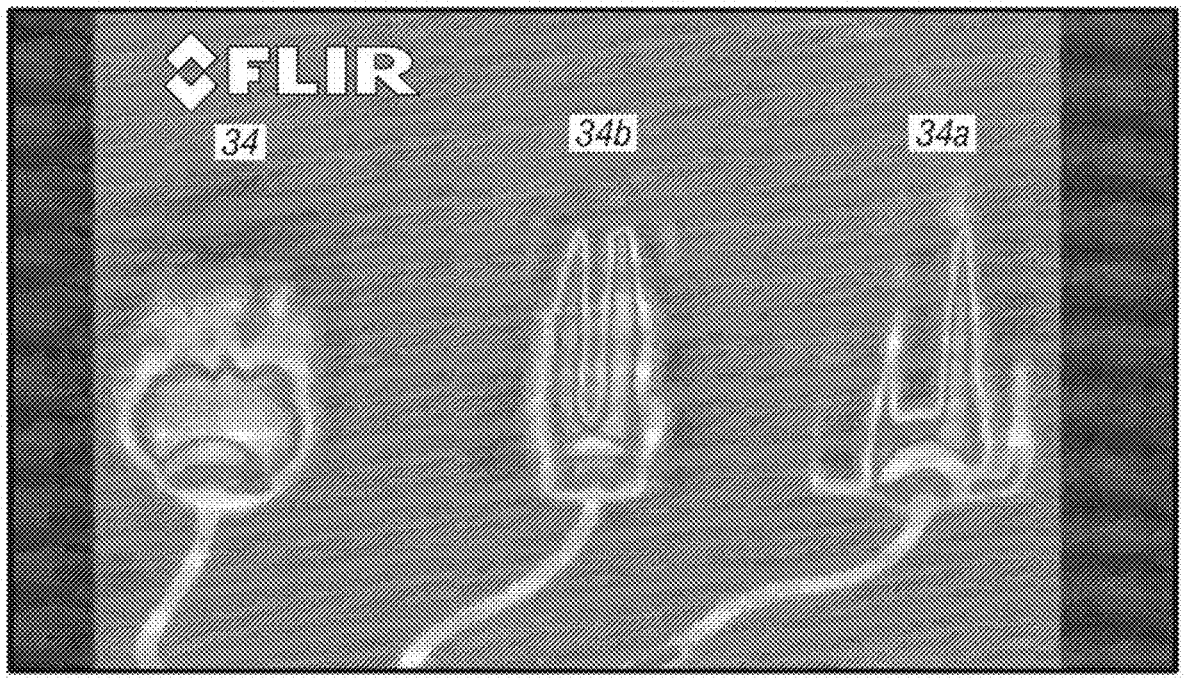

FIGS. 8A and 8B illustrate the improved wicking or "wetting" properties of the present wound inserts. More particularly, forward-looking infrared (FLIR) images are shown in FIG. 8A of a traditional wound insert 34, a wound insert 34a formed from foam 300 (having a trapezoidal or tapered squaretooth configuration) of FIG. 4, and a wound insert 34b formed in similar fashion from foam 350 (having a triangular sawtooth configuration) of FIG. 5. FIG. 8A shows the wound inserts at an initial time before fluid is delivered to the lower ends of each of the wound inserts 34, 34a, and 34b; and FIG. 8B shows the wound inserts after fluid has been delivered to the lower ends of each of the wound inserts 34, 34a, and 34b. As shown, the present wound inserts 34a and 34b wick fluid away from their lower ends, and through their respective lengths, more quickly than the traditional wound insert 34. This improved wicking of the present wound inserts may be even more pronounced where wound inserts 34a and 34b comprise hydrophilic foam or are coated with a hydrophilic coating. In some embodiments, thick portions 304, thin portions 308, high-density regions 404, and/or low-density regions 408 can be coated and/or printed (either before or after compression) to enhance the hydrophilic or hydrophobic properties of individual regions of the foam or of the foam as a whole. Such coated regions may also contain and/or be coated with other additives, such as antibiotics, or blockage-reducing agents.

Figure 10:
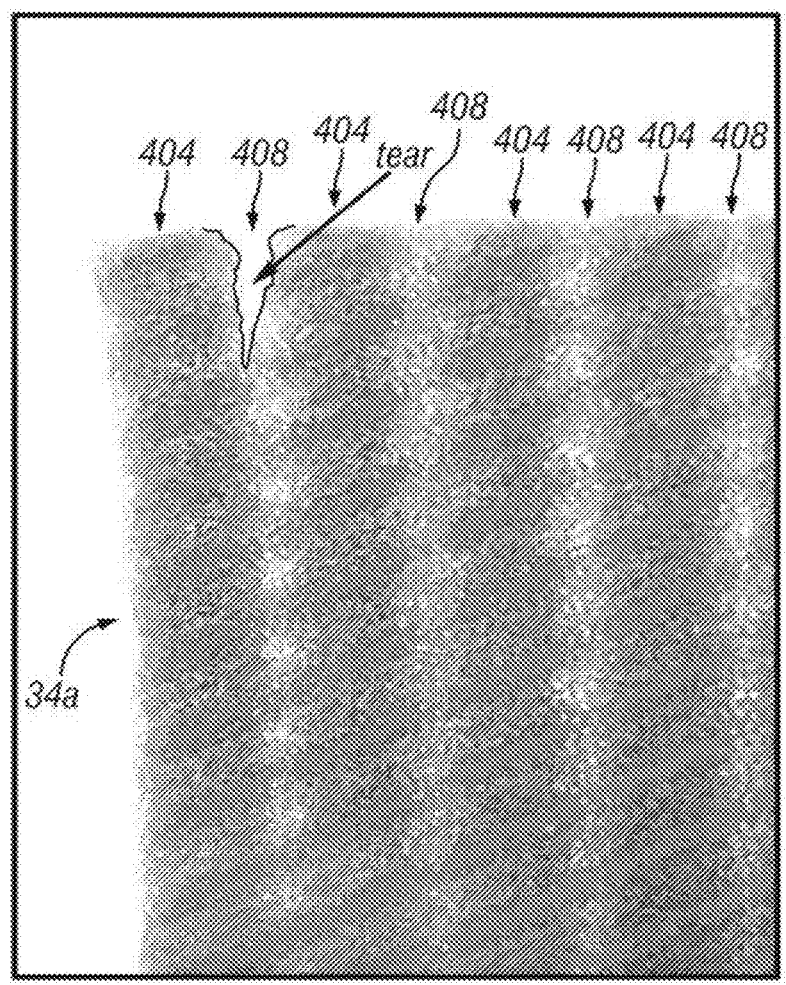
FIG. 10 depicts a top view of an embodiment of the present wound inserts illustrating tearing of the wound insert along a lower-density region.
Figure 11:
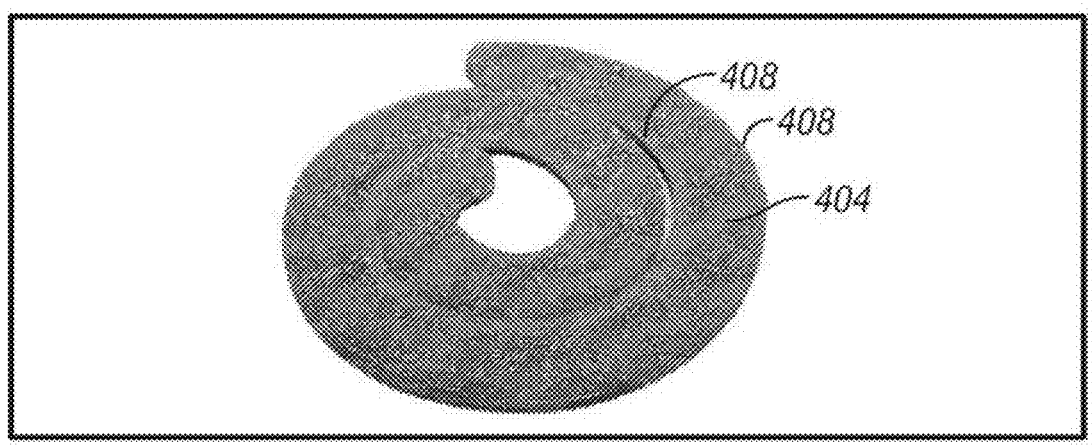
FIG. 11 depicts an embodiment of one of the present wound inserts in a circular configuration.

Referring now to FIGS. 10-11, embodiments are shown of the present wound inserts illustrating additional features of the present wound inserts. FIG. 10 illustrates a photograph of a top view of wound insert 34. Wound insert 34 is configured to have anisotropic properties. More particularly, high-density regions 404 have a greater tensile strength than low-density regions 408 such that wound insert can be torn along low-density regions 408, as shown. More specifically, when a tearing force is applied to wound insert 34 (e.g., by pulling two high-density regions 404 in directions away from one another), the foam is more likely to tear along a low-density region 408 between the high-density regions than in any other direction. As such, the low-density regions 408 can be described as zones of relative weakness that permit directional tearing without having to separately perforate the foam (e.g., reducing manufacturing costs and complexity, and eliminating the debris that may be formed by perforating processes). While low-density regions 408 are provided in rows in the embodiments shown, in other embodiments low-density regions can be provided in any suitable configuration. For example, the present wound inserts can comprise low-density regions 408 and high-density regions 404 in alternating, sequentially larger rectangles (e.g., squares), rings (e.g., circles), or a checker-board pattern.

FIG. 11 shows a photograph of a portion of wound insert 34a, and more-particularly, shows a high-density region 404 that has been torn or otherwise separated to include a single high-density region 404 and portions of the adjacent low-density regions 408 adjoining the high-density region 404. As shown, the high density region 408 is mechanically strong and/or durable enough to be compressed into various shapes. For example, in the embodiment shown, high-density region 404 has been spiraled into a circular configuration. Additionally, a single high-density region 404 (and adjoining portions of the adjacent low-density regions) can be torn or otherwise removed from a wound insert 34, such that the high-density region 404 can be inserted into a tunnel-type wound, and/or removed from a tunnel-type wound without breaking the foam and/or losing particles of foam in the wound.

Some embodiments of the present wound dressings comprise a wound dressing (e.g., any of the present wound dressings, such as 34a, 34b) configured to be positioned on a wound (e.g., 26) of a patient (e.g., 30) and/or on or in contact with the wound surface (e.g., 42), where the wound insert comprises a foam (e.g., 300) having high-density regions (e.g., 404) and low-density regions (e.g., 408) having a density that is less than the density of the high-density regions. In some embodiments, the foam is sterile (e.g., substantially free of microbes and/or bacteria). Some embodiments further comprise a drape (e.g., 38) configured to be coupled to skin (e.g., 46) of the patient such that the drape covers the wound insert and the wound, and forms a space between the drape and the wound (e.g., in a manner such as that shown in FIG. 1).

Some embodiments of the present wound-treatment methods comprise: positioning a wound insert (e.g., any of the present wound inserts such as 34a, 34b) on a wound (e.g., 26) of a patient (e.g., 30), where the wound insert comprises a foam (e.g., 300) having high-density regions (e.g., 404) and low-density regions (e.g., 408) having a density that is less than the density of the high-density regions. In some embodiments, the foam is sterile (e.g., substantially free of microbes and/or bacteria). Some embodiments further comprise: coupling a drape (e.g., 38) to skin (e.g., 46) adjacent the wound such that the drape covers the wound insert and the wound, and forms a space between the drape and the wound. Some embodiments comprise: applying negative pressure to the wound through the wound dressing (e.g., through the wound insert). In some embodiments, applying negative pressure to the wound comprises activating a vacuum source (e.g., apparatus 14 of FIG. 1, or vacuum source 200 of FIG. 3) that is coupled to the wound dressing. Some embodiments comprise: delivering a fluid to the wound through the wound dressing. In some embodiments, delivering a fluid comprises activating a fluid source (e.g., fluid source 248 of FIG. 3) that is coupled to the wound dressing.

Some embodiments of the present wound-treatment systems comprise either embodiment of system 10 (or any subset of components of either embodiment of system 10), and one or more of the present wound inserts and/or wound dressings.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this invention.

The invention claimed is:

1. A wound insert for use with a wound dressing, the wound insert comprising:
   a foam having high-density regions and low-density regions, the high-density regions having a density of between 1.2 to 4 times the density of the low-density regions; and
   a drape for coupling to skin of a patient adjacent a wound to which the wound dressing is applied such that the drape covers the wound insert and the wound, and forms a space between the drape and the wound.

2. The wound insert of claim 1, wherein the foam comprises a hydrophilic foam.

3. The wound insert of claim 1, wherein the high-density regions and low-density regions are configured in alternating rows.

4. The wound insert of claim 1, wherein the high-density regions and low-density regions are configured in a grid pattern.

5. The wound insert of claim 1, wherein the low-density regions have a density that is less than a density of the high-density regions when the foam is positioned in a compressed configuration.

6. The wound insert of claim 1, wherein the high-density regions are configured to contract less under negative pressure than the low-density regions under the negative pressure.

* * * * *